United States Patent [19]

O'Sullivan et al.

[11] 3,931,678

[45] Jan. 13, 1976

[54] DENTAL FILLING METHOD AND COMPOSITION FORMED THEREBY

[75] Inventors: Denis J. O'Sullivan; T. Eisirt Casey, both of Dublin, Ireland

[73] Assignee: Loctite (Ireland) Limited, Dublin, Ireland

[22] Filed: Sept. 24, 1974

[21] Appl. No.: 503,992

[52] U.S. Cl. .................................................. 32/15
[51] Int. Cl.² ........................................ A61K 5/02
[58] Field of Search .................................... 32/15

[56] References Cited
UNITED STATES PATENTS

| | | | |
|---|---|---|---|
| 3,635,889 | 1/1972 | Bowen | 32/15 |
| 3,814,717 | 6/1974 | Wilson | 32/15 |

Primary Examiner—Robert Peshock
Attorney, Agent, or Firm—Jean B. Mauro; J. Rodney Reck

[57] ABSTRACT

A process for repairing dental caries which comprises:
  a. Removing decayed tooth structure to form a dental cavity;
  b. Filling said cavity with a dental filling composition comprising
    1. A free-radical polymerizable acrylate monomer;
    2. A free radical polymerization initiator; and
    3. An inorganic filler;
  c. Applying an aqueous solution of waterglass to the surface of the composition and allowing the water to evaporate to leave a solid, essentially oxygen-impermeable coating of waterglass;
  d. Permitting said composition to harden to form a restored dental surface; and
  e. Washing off the waterglass coating with water.

7 Claims, No Drawings

DENTAL FILLING METHOD AND COMPOSITION FORMED THEREBY

BACKGROUND OF THE INVENTION

This invention relates to a novel process for filling dental cavities. Co-pending application Ser. No. 415,454, filed Nov. 12, 1973, by the inventors hereof relates to an improved dental filling composition comprising certain monomeric compositions which are described in detail herein. Briefly, these compositions comprise polymerizable urethane-acrylate resins which cure by a free-radical mechanism, along with a free-radical initiator. While these compositions do function well for their intended purpose, because of the polymerization inhibiting effect of oxygen on compositions of this nature, the surface cure of the compositions when applied to a dental cavity is sometimes not reliably completed. It has now been found that surface cure properties can be improved by use of the present process.

SUMMARY OF THE INVENTION

This invention deals with a novel process for sealing the surface of a composition for dental filling, which composition utilizes a polymerizable acrylate monomer, preferably a urethane-acrylate monomer containing at least two reactive acrylic functional groups and at least two urethane linkages per molecule. It has been found that a monomer of this preferred type, when polymerized in situ in a dental application of the type described herein, will produce a polymer which has superior properties as a tooth filling. Polymerization is induced by a free-radical method, involving either the use of an ultra-violet (hereinafter "UV") activated free-radical generator, or a peroxy compound in combination with a known activator for said peroxy compound. The composition may also be incorporated into a dental filling composite which utilizes the above-described urethane-acrylate monomer and curing agents, in combination with an inorganic filling material. This composition or composite is applied to a dental cavity which has been prepared according to standard techniques of dentistry.

The novel feature of the present invention involves application to the composition or composite described above of an aqueous solution of waterglass, i.e., sodium metasilicate, $Na_2SiO_3$. The water is allowed to evaporate leaving a solid film or coating of sodium metasilicate which is essentially impermeable to oxygen. Thus, oxygen is excluded from the surface of the curable composition, thereby permitting the surface to cure fully. The waterglass film is then readily washed away by rinsing with water.

The invention also involves a composition comprising a curable dental filling composition or composite having a waterglass coating thereon.

DETAILED DESCRIPTION OF THE INVENTION

The critical feature of the invention is the creation of an essentially oxygen-impermeable film over the surface of the curable filling composite or composition. Theoretically, any material which is capable of forming such a film in the environment of the mouth should be suitable provided it does not mix with or adsorb the filling material, can be easily removed without damaging the cured surface, and is non-toxic. Preferably, such material is inorganic. Water-soluble organic polymers such as polyvinyl alcohol and its copolymers with polyvinyl chloride are not recommended.

It has been found that most desirable material for this purpose is waterglass, i.e., sodium metasilicate, $Na_2SiO_3$. This material appears to be virtually unique in its exceptional ability to meet all the criteria described in the preceeding paragraph. Waterglass is bland and non-toxic and will not mix with the curable monomer. It also has the very desirable property of being highly water soluble, which facilitates its application and permits easy removal. This property also permits the waterglass film to be readily and completely removed from the cured surface of the filling material by merely rinsing with water, preferably tepid water. Useful concentrations of waterglass are in the range of approximately 25 to 60 per cent by weight of the aqueous solution. The lower concentrations are preferred because of their relatively low viscosity. The preferred concentration range is approximately 30 to 55 per cent by weight.

It is also desirable to include in the waterglass solution a small amount of a surface active agent which serves to improve the wetting properties of the sodium metasilicate solution, thereby enhancing its ability to cover the filling material. Obviously, the surface active agent should be non-toxic. Theoretically, any non-ionic surface active agent with adequate wetting properties can be used; however, the sulfates, sulfonates, phosphates, or mixtures of these are preferred. Useful surface active agent concentrations range from approximately 0.05 to approximately 1 per cent by weight of the aqueous solution, preferably approximately 0.1 to approximately 0.5 per cent by weight.

The waterglass solution can be applied to the composition or composite surface by any convenient means such as painting or spraying.

In general, any free-radical polymerizable acrylate monomer can be used in this invention, provided that it is otherwise acceptable for dental use. It is known in the art that the polymerization of such monomers tends to be inhibited to some extent by the presence of air or oxygen, thus resulting in incomplete cure at the exposed surface of the polymerizing mass. This problem is solved by the present invention by covering such surface with an oxygen-excluding film or coating of waterglass.

The urethane-acrylate monomers preferably used in the compositions and process of this invention are substances having structures which allow them to be regarded as the reaction product of an organic polyisocyanate with a polymerizable acrylate ester having a hydroxy or a primary or secondary amino group in the alcoholic moiety thereof. The active ydrogen atom in the alcoholic portion of the ester reacts with the isocyanate group, producing the polymerizable urethane-acrylate monomer used herein.

It is understood that certain of these monomers may, in fact, be oligomers or other low polymers of the urethane-acrylate monomer which contain at least two acrylic functional groups, and all such materials are considered to meet the definition of urethane-acrylate monomer as discussed and used herein. Suitable monomers are disclosed in U.S. Pat. No. 3,425,988 to Gorman et al.

The acrylates which may be used in making the urethane-acrylate monomer are substances of the general formula $$CH_2=CR^2 . COOR^3 \qquad (1)$$

in which $R^2$ is H, $CH_3$, $C_2H_5$ or Cl and $R^3$ is one of the following: (a) a $C_{1-8}$ hydroxyalkyl or aminoalkyl group, (b) a $C_{1-6}$ alkylamino-$C_{1-8}$ alkyl group; or (c) a hydroxyphenyl, an aminophenyl, a hydroxynaphthyl or an aminonaphthyl group which may be further substituted by an alkyl, alkylamino or dialkylamino group, each alkyl group in this sub-part (c) containing up to about 3 carbon atoms.

These acrylates are exemplified by, but not limited to, 2-hydroxyethyl acrylate, 2-hydroxyethyl methacrylate, 2-aminopropyl methacrylate, hydroxyhexyl acrylate, 2-tert-butylaminoethyl methacrylate and hydroxyoctyl methacrylate.

In a convenient and known process for making the polymerizable monomer used in the polymerizable composition according to this invention, an acrylate of general formula I is reacted with a di- or other polyisocyanate, preferably in the presence of a solvent, at a temperature in the range of 0°–200°C as will be described in more detail later, chosen to suit the specific reactants involved.

The polyisocyanates which may be used in making the polymerizable monomer may be generally represented by the formula $(O=C=N)_nQ$, in which n is an integer from 2 to about 20, preferably 2 to about 5, and Q is an organic radical having a molecular weight up to about 5000 and a bonding capacity equal to n. A preferred class of isocyanates are those of the formula:

   (II)

wherein $n$ is 2 and $R^4$ is a $C_{2-20}$ alkylene, alkylene or cycloalkylene radical or a $C_{6-40}$ arylene, alkarylene, aralkarylene, alkyloxyalkylene or aryloxyarylene radical which may be substituted by 1–4 chlorine atoms or by 1–3 amino or mono- or di-$C_{1-3}$-alkylamino or $C_{1-3}$ alkoxy groups.

Typical examples of such isocyanates are toluene diisocyanates, 4,4′-diphenyl diisocyanate, 4,4′-diphenyl methane diisocyanate, dianisidine diisocyanates, 1,5-naphthalene diisocyanate, 4,4′-diphenyl ether diisocyanate, p-phenylene diisocyanate, trimethylene diisocyanate, tetramethylene diisocyanate, hexamethylene diisocyanate, ethylene diisocyanate, cyclohexylene diisocyanates, nonamethylene diisocyanate, octadecamethylene diisocyanate, 2-chloropropane diisocyanate, 2,2′-diethyl-ether diisocyanate, 2-(dimethylamino) pentane diisocyanate, tetrachlorophenylene-1,4-diisocyanate, 3-heptene diisocyanate and trans-vinylene diisocyanate.

Other polyisocyanates which may be used are the higher molecular weight polyisocyanates obtained by reacting polyamines containing terminal primary or secondary amine groups, or polyhydric alcohols, for example, the alkane and alkene polyols such as glycerol, 1,2,6-hexanetriol, 1,5-pentenediol, ethylene glycol, polyethylene glycol, "bisphenol-A" and substituted bisphenol-A, with an excess of any of the above-named diisocyanates. These higher molecular weight urethane or ureide polyisocyanates may be represented by the formula:

   (III)

in which $R^4$ has the meaning given above; X represents O or $NR^6$ where $R^6$ is H or a $C_{1-7}$ alkyl group; and $R^5$ is the non-functional residue of a polyamine or a polyhydric alcohol having at least n primary or secondary amino or hydroxyl groups respectively; and n is an integer from 2 to 20.

Accordingly, when the monomer is derived from one of the simple diisocyanates defined above, it has the general formula:

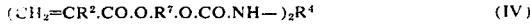   (IV)

in which $R^2$ and $R^4$ have the meanings given above and $R^7$ represents $R^3$ less one hydrogen atom. Preferred monomers conforming to this definition include derivatives of higher alkylene diisocyanates such as octamethylene diisocyanate, and the aromatic diisocyanates containing more than 8 non-isocyanate-group carbon atoms, such as durene diisocyanate, i.e., tetramethylphenyl-1,4 diisocyanate, and 4,4′-diphenyl diisocyanate. When, on the other hand, the monomer is derived from one of the higher molecular weight urethane or ureide polyisocyanates aforesaid, it has the general formula:

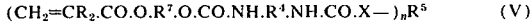   (V)

in which $R^2$, $R^4$, $R^5$, $R^7$, X and n have the meanings given above.

As used herein, the term urethane denotes a compound having in the molecule the characteristic group —O—CO—NH— and the term ureide denotes a compound having in the molecule the characteristic group —NH—CO—NH—.

A typical and preferred monomer useful in the polymerizable composition of this invention is the monomer of formula IV in which $R^2$ is $CH_3$, $R^7$ is n-$C_3H_6$ and $R^4$ is

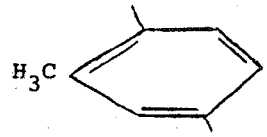

An acrylate is, as stated above, reacted with a polyisocyanate to form a monomer for use in the polymerizable composition of the invention. While the proportions of the reactants used are not critical, it is generally preferred to use about a 0.1 equivalent excess of polyisocyanate above the amount needed to furnish one isocyanate group for each hydroxyl or amino group in the acrylate molecule.

The reaction may be carried out in the presence or absence of a solvent. Preferably solvents selected from the aliphatic, cycloaliphatic and aromatic hydrocarbons, for example, benzene, toluene, cyclohexane, hexane and heptane, are employed, but other solvents such as methyl isobutyl ketone, diamyl ketone, isobutyl methacrylate, and cyclohexyl methacrylate can also be utilized if desired, especially where complete compatibility with the dental adhesive is desired. The chief reason for using a solvent is to prevent the reaction mixture from becoming too viscous.

The temperature employed in the reaction may vary over a wide range. Where the reactants are present in approximate chemically equivalent amounts or with slight excess of the isocyanate reactant, useful temperatures lie in a range extending from about 10° to 175°C.

When the simpler isocyanates are used the reactants are preferably at or near room temperature, e.g., from 20°C to 30°C. In the preparation of the high molecular weight monomers using an excess of the isocyanate, the reactants may be combined at room temperature but it is preferable to allow them to react at a temperature in the range 40° to 150°C, a specially preferred range having been found to extend from 90° to 120°C. Further detail may be found in U.S. Pat. No. 3,425,988.

Reaction proceeds with a slight elevation of the temperature and is complete when heat ceases to be evolved. The reaction mixture is then cooled at room temperature; if the solvent used is suitable for incorporation in the polymerizable composition according to this invention, the reaction product will need no extraction or purification and is ready for use.

To provide the necessary curing ability to the above-described urethane-acrylate monomer, a suitable initiator system is used in conjunction therewith. If the monomer is to be cured by a uv activation mechanism, a uv activated free-radical generator is selected, and generally may be incorporated directly into the urethane-acrylate monomer. For example, it is possible to use a metal carbonyl of the formula $M_x(CO)_y$, wherein M is a metal atom, preferably Cr, Mn, Fe, Co, Ni or Mo, $x$ is 1 or 2, and $y$ is an integer determined by the total valence of the metal atoms, generally from 4 to 10. The preferred uv activated free-radical generators are selected from: (a) $C_{1-16}$ straight or branched chain alkyl diones; and (b) carbonyl compounds of the general formula:

$$R(CO)R^1$$

in which R is a $C_{1-10}$ alkyl, aryl, aralkyl or alkaryl radical, and $R^1$ is R or H. R or $R^1$ can contain any substituents which do not adversely affect the compound in serving its intended function. For example, R or $R^1$ can be alpha-substituted with an alkyl, aryl, alkaryl alkoxy or aryloxy radical, or with an amino or a mono- or dialkylamino derivative thereof, each of the above substituents containing up to about six carbon atoms. In addition, R and $R^1$, taken together with the carbonyl group to which they are attached, may represent an aromatic or heterocyclic ketone containing up to about sixteen (16) carbon atoms.

Preferred polymerization initiators are acetophenone, benzophenone and 1- and 2- acetonaphtone. Others are 2,3-butadione, 2,4-dimethyl-3-pentanone, 1- and 2-naphthaldehyde, p-phenylacetophenone, n-proprionophenone, fluoren-9-one, xanthen-9-one and 4,4'-bis-dimethylaminobenzophenone. Uv initiators generally are used at a level between about 0.1 and 10 percent by weight of the urethane-acrylate monomer, and preferably between about 1.5 and 7.5 percent by weight.

When cure is to be initiated by free-radical mechanism which is not uv dependent, the urethane-acrylate monomer is used in combination with a peroxy compound and an activator for said peroxy compound. The specific peroxy compound and activator therefor are determined by the speed of cure desired in the final dental sealing or filling composition. This speed of cure also can be varied by the appropriate balancing of concentrations of monomer, peroxy compound and activator therefor. Organic hydroperoxides and organic peresters can be used in the compositions and processes of this invention, particularly those having a molecular weight between about 90 and about 800, preferably between 90 and 400. Typical examples are t-butylperbenzoate, cumene hydroperoxide and t-butylhydroperoxide. These initiators generally are used at a level between about 0.5 and 10 percent by weight of the urethane-acrylate monomer, preferably 1 to 5 percent by weight.

The peroxy compounds of the preceding paragraph frequently can be activated by the use of organic sulfimides (such as benzoic sulfimide) and/or primary, secondary or tertiary amines (preferably those to be described hereafter). Typically, these activators are used at a level between about 0.1 and about 7 percent by weight of the urethane-acrylate monomer, preferably 0.2 to 4 percent by weight. Alternatively, low levels of transition metal compounds frequently can be used, commonly at a level between about 1 and 1000 parts per million by weight of the urethane-acrylate monomer. Most typically the transition metal is selected from the class consisting of copper, iron, manganese and cobalt.

The most highly preferred peroxy initiator system is obtained by the use of a peroxy initiator selected from the class consisting of acyl peroxides and silyl peroxides. The acyl peroxides have the general formula:

$$Ar.CO.O_2.CO.Ar$$

where each Ar is an aryl radical containing up to about 10 carbon atoms and preferably is $C_6H_5$, $ClC_6H_4$, $NO_2C_6H_4$, or $Cl_2C_6H_3$. The silyl peroxides have the general formula:

$$CH_2=CH-Si(OOR^8)_3$$

in which $R^8$ is a $C_{1-6}$ straight or branched chain alkyl radical. The preferred compounds from each group are benzoyl peroxide and vinyl tris(tert-butyl peroxy)silane, respectively. The most highly preferred class is the acyl peroxides. The peroxides of this paragraph generally are used at a level between about 0.05 and 5 percent by weight of the urethane-acrylate monomer, preferably 0.1 to 3 percent by weight.

The peroxides of the preceding paragraph, and most particularly the acyl peroxides, are most commonly activated by the use of an organic amine, generally having a molecular weight less than about 800. While primary, secondary or tertiary alkyl, aryl or alkyl/aryl amines can be used, the preferred amines are amines of the formula:

$$ArNR^9R^{10}$$

where Ar is as defined above, preferably being $C_6H_5$ or a $C_1$-$C_4$ alkyl substituted $C_6H_5$; and each of $R^9$ and $R^{10}$ is hydrogen or a $C_1$ to $C_4$ alkyl group. Preferably each of $R^9$ and $R^{10}$ is methyl or ethyl.

The amines are used at the same level described in the preceding paragraph for the peroxides. In addition to the above ingredients, other ingredients known in the dental filling composition art may be added. The common additive, and one which is essential in most dental filling compositions, is an inorganic filler material, such as finely ground glass powder. The preferred filler is an aluminum borosilicate glass, most preferably having an average particle size which is less than about 40 microns. The inorganic filler frequently comprises a significant, and even a major, portion of dental filling composites. For example, they can comprise from about 40 to about 95 percent by weight of the total composition, preferably 70 to 90 percent by weight.

It is frequently desirable to add low levels, such as up to about 500 parts per million by weight, of a free-radical or uv stabilizer, many of which are shown in the art, to prevent spurious polymerization of the composition prior to the time of its intended use. Suitable free-radical stabilizers are hydroquinone, p-benzoquinone, butylate of hydroxy toluene and butylate of hydroxyanisole. It also may be desirable to modify the compositions by the addition of lower viscosity polymerizable ingredients, most commonly lower viscosity acrylate esters. Typical examples are hydroxyethyl methacrylate, hydroxypropyl methacrylate, trimethylolpropane trimethacrylate, butyleneglycol dimethacrylate and polyethyleneglycol dimethacrylate. Many other acrylate esters are known in the art, and essentially any of said esters can be used for purposes herein. An amount of lower viscosity acrylate ester is used which is necessary to produce the desired viscosity, but when the ester selected contains only one acrylic functional group, the amount used should not exceed the weight of the urethane-acrylate ester since the hardness or durability of the final product could be affected.

Other materials, such as adhesive agents, plasticizers, pigmenting agents, etc., can be used if desired.

In discussing the use ratios of the various components, the bulk of the composition should be composed of at least 5% by weight urethane acrylate monomer, plus initiator system and inorganic filler. All other ingredients preferably do not comprise more than about 30 percent by weight of the composition.

For a system which is to be initiated by a uv mechanism, it is generally preferable to add the uv activated free-radical initiator directly to the mixture of urethane acrylate monomer and other ingredients as described herein. This provides a one-component system which can be used directly to fill the apertures or cavities in the teeth and immediately activated with uv light. In those systems which are not to be uv activated, it is possible to prepare systems which can contain all necessary curing agents as a single component composition, such as one in which the cure is via a hydroperoxide/amine initiator system. Such one-component peroxy systems tend to be excessively slow; a far more preferable approach is to separate either the peroxy compound or the activator therefor into a second component which is to be added immediately prior to use. In this fashion, compounds can be selected and used in such amount as to provide much more rapid cure. It is for this reason that a certain number of systems enumerated above have been specified as preferred compositions.

When the two-component system is to be utilized, it is preferable that the peroxy compound be used as an additive at the time of use since in this way the most highly stable compositions can be prepared. The dentist then can measure out the appropriate quantities of each of the two components and mix them, directly apply them to the aperture or cavity, and within a short time such as one to 30 minutes, a hard and durable filling composition will be formed in the tooth. When the two-component system is utilized, it is generally desirable to mix the peroxy ingredient with a plasticizer or a polymerizable acrylate ester, including a urethane acrylate monomer, to facilitate mixing at the time of use. The balance of weight of use between the two components is a matter of choice dependent upon the systems used, and determination thereof is well within the province of the reasonably skilled chemist.

The compositions of this invention have been found to be easily prepared and used. When placed and cured in a tooth cavity, the composition forms hard and durable adhesive bonds to normal tooth structure. The cured composition is abrasion resistant, and can easily be formulated to match the tooth color and texture.

EXAMPLES

The invention will now be illustrated by the following description of specific embodiments thereof, given by way of example only.

The monomers used in the Examples are monomers A and B, and have the formulae:

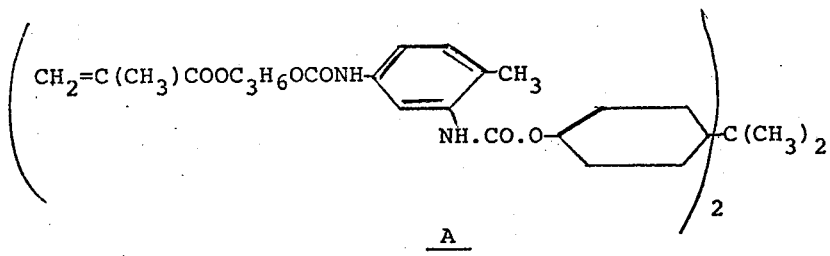

and

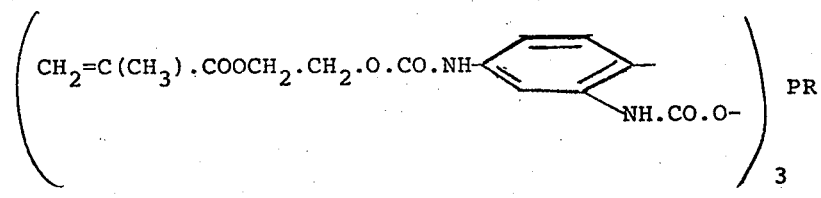

in which PR represents a propylene triol oligomer (average molecular weight 2500) devoid of its three hydroxyl groups.

EXAMPLE I

A dental filling composition was prepared by blending the following ingredients, expressed on a parts by weight basis:

| 1 | Monomer A | 14 |
|---|---|---|
| 2 | Monomer B | 7 |
| 3 | Methacrylic Acid | 0.8 |
| 4 | Methacryloxy trimethoxysilane | 0.66 |
| 5 | Naphthoquinone 0.33 | |
| 6 | Cumene hydroperoxide | 0.166 |
| 7 | Benzophenone | 1.6 |

-continued

| 8  | Hydroxyethyl methacrylate        | 14  |
| 9  | Uniflex 330                      | 15  |
| 10 | Glass powder (dental quality) q.s.ad. | 100 |

Ingredients 3 and 4 are adhesion promoters, 5 is a stabilizer, 6 is a free-radical inhibitor, 7 is the photoinitiated carbonyl compound, 8 and 9 are viscosity regulators, 9 being a proprietary product of Union Camp Corporation, Wayne, N.J. which comprises poly(butylene sebacate), and 10 is a mechanical extender and toughener as used in conventional dental filling compositions.

The composition was applied to a prepared tooth cavity, molded into the required shape, and painted with a solution made up as follows:

| Waterglass    | 100 ml (as 54% by weight aqueous solution) |
| "Neutrobrite" | 0.5 gm |
| Water         | 50 ml |

In this formulation the water acts as a diluent and viscosity modifier. "Neutrobrite" is the trade name of a mixture of sodium hexametaphosphate and sodium lauryl sulfate sold by Albright & Wilson, Ltd.. The water was allowed to evaporate, leaving a film of waterglass.

The covered composition was then irradiated for 60 seconds at 12 inches diatance using a lighted Philips 125 watt HPK high pressure mercury vapor ultraviolet-emitting lamp. Under this treatment the composition rapidly cured, yielding a highly satisfactory dental filling. The waterglass film was then readily removed by rinsing with tepid water, leaving the filling intact.

EXAMPLE II

A two-part dental filling composition was prepared using the following ingredients, expressed as parts by weight:

FIRST PART

| 1.  | Monomer A                  | 14   |
| 2.  | Monomer B                  | 8    |
| 3.  | Methacrylic acid           | 1    |
| 4.  | Methacryloxy trimethoxysilane | 0.66 |
| 5.  | Naphthoquinone             | 0.3  |
| 6.  | N,N-dimethyl-p-toluidine   | 0.5  |
| 7.  | Hydroxypropyl methacrylate | 14   |
| 8.  | Uniflex 330                | 10   |
| 9.  | Glass Powder, q.s.ad.      | 100  |

SECOND PART

| 10. | Dibenzoyl peroxide | 5  |
| 11. | Uniflex 330        | 45 |
| 12. | Glass Powder       | 50 |

Ten parts by weight of the First Part were mixed with one part by weight of the Second Part. The mixture was applied to a prepared tooth cavity, where it was molded into the desired shape. The waterglass solution of Example I was then applied and the water was permitted to evaporate. After several minutes the filling was sufficiently hard for normal use, and was a highly satisfactory dental filling by standard professional criteria. The waterglass film was removed by rinsing with tepid water, leaving the filling intact.

We claim:

1. A process for repairing dental caries which comprises:
    a. Removing decayed tooth structure to form a dental cavity;
    b. Filling said cavity with a dental filling composition comprising
        1. a urethane-acrylate monomer formed by the reaction of an organic polyisocyanate with a polymerizable acrylate ester having a hydroxy or amino group in the alcoholic moiety thereof;
        2. a free-radical polymerization initiator; and
        3. an inorganic filler;
    c. Applying an aqueous solution of about 25 percent to about 60 percent by weight waterglass to the surface of the composition and allowing the water to evaporate to leave a solid, essentially oxygen-impermeable coating of waterglass;
    d. Permitting said composition to harden to form a restored dental surface; and
    e. Washing off the waterglass coating with water.

2. The process of claim 1 in which the aqueous waterglass solution also contains about 0.05 to about 1.0 percent by weight of a water-soluble surface active agent.

3. The process of claim 2 wherein the acrylate ester has the formula $CH_2=CR^2.COOR^3$ wherein $R^2$ is H, $CH_3$, $C_2H_5$ or Cl and $R^3$ is one of the following: (a) a $C_{1-8}$ hydroxyalkyl or aminoalkyl group, (b) a $C_{1-6}$ alkylamino-$C_{1-8}$ alkyl group; or (c) a hydroxyphenyl, an aminophenyl, a hydroxynaphthyl or an aminonaphthyl group which may be further substituted by an alkyl, alkylamino or dialkylamino group, each alkyl group in this sub-part (c) containing up to about 3 carbon atoms.

4. The process of claim 3 wherein the polyisocyanate has the formula $(O=C=N)_nR^4$ wherein $n$ is 2 and $R^4$ is a $C_{2-20}$ alkylene, alkenylene or cycloalkylene radical or a $C_{6-40}$ arylene, alkarylene, aralkarylene, alkyloxyalkylene or aryloxyarylene radical which may be substituted by 1-4 chlorine atoms or by 1-3 amino or mono- or di-$C_{1-3}$-alkylamino or $C_{1-3}$ alkoxy groups.

5. The process of claim 4 wherein the free-radical polymerization initiator is a UV activated free-radical generator selected from: (a) $C_{1-16}$ straight or branched chain alkyl diones; and (b) carbonyl compounds of the general formula $R(CO)R^1$ in which R is a $C_{1-10}$ alkyl, aryl, aralkyl or alkaryl radical, and $R^1$ is R or H.

6. The process of claim 4 wherein the free-radical polymerization initiator is a peroxy initiator selected from (a) acyl peroxides of the formula $ArC(O)O_2C(O)Ar$ wherein each Ar is an aryl radical containing up to about 10 carbon atoms and (b) silyl peroxides of the formula $CH_2=CH-Si(OOR^8)_3$ wherein each $R^8$ is a $C_1$ to $C_6$ alkyl radical.

7. A process for repairing dental caries which comprises:
    a. Removing decayed tooth structure to form a dental cavity;
    b. Filling said cavity with a dental filling composition comprising
        1. a free-radical polymerizable acrylate monomer;
        2. a free-radical polymerization initiator; and
        3. an inorganic filler;
    c. Applying an aqueous solution of waterglass to the surface of the composition and allowing the water to evaporate to leave a solid, essentially oxygen-impermeable coating of waterglass;
    d. Permitting said composition to harden to form a restored dental surface; and
    e. Washing off the waterglass coating with water.

* * * * *

UNITED STATES PATENT OFFICE
CERTIFICATE OF CORRECTION

PATENT NO. : 3,931,678
DATED : January 13, 1976
INVENTOR(S) : Denis J. O'Sullivan & T. Eisirt Casey It is certified that error appears in the above-identified patent and that said Letters Patent are hereby corrected as shown below:

In column 2, line 3 - after the word "that" and before the word "most" insert the word -- the --.

In column 3, line 33 - delete the word "alkylene" second occurrence and insert the word -- alkenylene --.

In column 8, line 67 - the number "0.33" should occur in the corresponding blank space in the righthand column.

In column 9, line 29 - delete the word "diatance" and insert the word -- distance --.

Signed and Sealed this

First Day of March 1977

[SEAL]

Attest:

RUTH C. MASON
*Attesting Officer*

C. MARSHALL DANN
*Commissioner of Patents and Trademarks*